US00PP29907P3

(12) United States Plant Patent
Koot

(10) Patent No.: US PP29,907 P3
(45) Date of Patent: Nov. 27, 2018

(54) ***VERBENA* PLANT NAMED 'DUEMPAMECH'**

(50) Latin Name: *Verbena hybrida*
Varietal Denomination: Duempamech

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 42 days.

(21) Appl. No.: 15/530,813

(22) Filed: Mar. 3, 2017

(65) Prior Publication Data

US 2018/0255677 P1 Sep. 6, 2018

(51) Int. Cl.
*A01H 5/02* (2018.01)

(52) U.S. Cl.
USPC ..... Plt./308

(58) Field of Classification Search
USPC ..... Plt./263.1, 308
See application file for complete search history.

*Primary Examiner* — Keith O. Robinson
*Assistant Examiner* — Karen M Redden
(74) *Attorney, Agent, or Firm* — C. A. Whealy

(57) ABSTRACT

A new and distinct cultivar of *Verbena* plant named 'Duempamech', characterized by its compact, semi-upright and mounding plant habit; moderately vigorous growth habit; freely branching habit; early and freely flowering habit; and violet-colored flowers with white-colored centers; flowers held above and beyond the foliar plane in mounded umbels.

1 Drawing Sheet

Botanical designation: *Verbena hybrida.*
Cultivar denomination: 'DUEMPAMECH'.

BACKGROUND OF THE INVENTION

The present invention relates to a new and distinct cultivar of *Verbena* plant, botanically known as *Verbena hybrida* and hereinafter referred to by the name 'Duempamech'.

The new *Verbena* plant is a product of a planned breeding program conducted by the Inventor in Rheinberg, Germany. The objective of the breeding program is to create new compact and early-flowering *Verbena* plants with numerous large and attractive flowers.

The new *Verbena* plant originated from a cross-pollination made by the Inventor in July, 2014 in Rheinberg, Germany of a proprietary selection of *Verbena hybrida* identified as code number VV12-003831-001, not patented, as the female, or seed, parent with a proprietary selection of *Verbena hybrida* identified as code number VV12-003138-002, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2016.

Asexual reproduction of the new *Verbena* plant by terminal cuttings in a controlled greenhouse environment in Rheinberg, Germany since June, 2016 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duempamech'. These characteristics in combination distinguish 'Duempamech' as a new and distinct *Verbena* plant:

1. Compact, semi-upright and mounding plant habit.
2. Moderately vigorous growth habit.
3. Freely branching habit.
4. Early and freely flowering habit.
5. Violet-colored flowers with white-colored centers; flowers held above and beyond the foliar plane in mounded umbels.

Plants of the new *Verbena* differ from plants of the female parent selection primarily in plant habit as plants of the new *Verbena* are more compact than plants of the female parent selection. In addition, plants of the new *Verbena* and the female parent selection differ in flower color as flowers of plants of the female parent selection are lighter violet in color.

Plants of the new *Verbena* differ from plants of the male parent selection primarily in flower size as plants of the new *Verbena* have smaller flowers than plants of the male parent selection. In addition, plants of the new *Verbena* and the male parent selection differ in flower color as flowers of plants of the male parent selection are lighter violet in color.

Plants of the new *Verbena* can be compared to plants of the *Verbena hybrida* 'Usbenal8', disclosed in U.S. Plant Pat. No. 14,853. In side-by-side comparisons, plants of the new *Verbena* differ primarily from plants of 'Usbenal8' in the following characteristics:

1. Plants of the new *Verbena* have smaller flowers than plants of 'Usbenal8'.
2. Plants of the new *Verbena* and 'Usbenal8' differ in flower color as flowers of plants of 'Usbenal8' are purple violet in color.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant.

The photograph is a side perspective view of a typical flowering plant of 'Duempamech'.

DETAILED BOTANICAL DESCRIPTION

The aforementioned photograph and following observations, measurements and values describe plants grown in 22-cm containers during the summer in a glass-covered greenhouse in Rheinberg, Germany and under cultural practices typical of commercial *Verbena* production. During the production of the plants, day and night temperatures averaged 18° C. and light levels averaged 4,500 lux. Plants were pinched one time three weeks after planting and were ten weeks old when the photograph and the description were taken. In the description, color references are made to The Royal Horticultural Society Colour Chart, 2007 Edition, except where general terms of ordinary dictionary significance are used.

Botanical classification: *Verbena hybrida* 'Duempamech'.

Parentage:

*Female, or seed, parent*.—Proprietary selection of *Verbena hybrida* identified as code number VV12-003831-001, not patented.

*Male, or pollen, parent*.—Proprietary selection of *Verbena hybrida* identified as code number VV12-003138-002, not patented.

Propagation:

*Type*.—Terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant habit*.—Compact, semi-upright and mounding plant habit; freely branching habit with about seven primary lateral branches with secondary lateral branches potentially forming at every node; pinching enhances lateral branch development; dense and bushy plant habit; moderately vigorous growth habit.

*Plant height*.—About 25 cm.

*Plant diameter*.—About 60 cm.

Lateral branch description:

*Length*.—About 35 cm.

*Diameter*.—About 4 mm.

*Internode length*.—About 2.8 cm.

*Texture*.—Pubescent.

*Strength*.—Strong.

*Color*.—Close to 144A.

Leaf description:

*Arrangement*.—Opposite, simple.

*Length*.—About 3.8 cm.

*Width*.—About 2.3 cm.

*Shape*.—Lanceolate.

*Apex*.—Acute.

*Base*.—Attenuate.

*Margin*.—Lobed.

*Texture, upper and lower surfaces*.—Pubescent, coarse.

*Venation pattern*.—Pinnate.

*Color*.—Developing leaves, upper surface: Close to 147A. Developing leaves, lower surface: Close to 147B. Fully expanded leaves, upper surface: Close to 146A; venation, close to 146A. Fully expanded leaves, lower surface: Close to 146B; venation, close to 146B.

*Petioles*.—Length: About 4.4 mm. Diameter: About 2.1 mm. Texture, upper and lower surfaces: Smooth, glabrous. Color, upper and lower surfaces: Close to 144C.

Flower description:

*Flower arrangement and habit*.—Salverform flowers arranged in hemispherical terminal umbels; umbels dense and mounding; numerous umbels per plant; flowers face upward or outwardly depending on position in the umbel; freely flowering habit with about 8 to 20 flowers per inflorescence and about 200 to 320 flowers developing per plant.

*Fragrance*.—None detected.

*Natural flowering season*.—Plants flower continuously from the spring through the fall in Germany; plants begin flowering about eight weeks after planting.

*Flower longevity*.—Individual flowers last about one week on the plant; flowers persistent.

*Inflorescence height*.—About 3.2 cm.

*Inflorescence diameter*.—About 5.6 cm.

*Flower buds*.—Length: About 1.3 cm. Diameter: About 2.8 mm. Shape: Oval to tubular. Color: Close to 89A.

*Flowers*.—Appearance: Salverform, five-parted fused corolla. Diameter: About 1.7 cm. Depth: About 2.1 cm. Throat diameter: About 1 mm. Tube length: About 1.7 cm.

*Corolla*.—Arrangement: Single whorl of five fused petals. Petal lobe length: About 8 mm. Petal lobe width: About 7 mm. Petal lobe shape: Obovate. Petal lobe apex: Emarginate. Petal margin: Entire. Petal texture, upper and lower surfaces: Smooth, glabrous. Throat texture: Smooth, glabrous. Tube texture: Smooth, glabrous. Color: Petal lobe, when opening, upper surface: Close to 88A; towards the base, close to NN155D. Petal lobe, when opening, lower surface: Close to 88B; towards the base, close to NN155D. Petal lobe, fully opened, upper surface: Close to 86B; towards the base, close to NN155D; main color becoming closer to 93A with development. Petal lobe, fully opened, lower surface: Close to 88C; towards the base, close to NN155D. Throat: Close to 145C. Tube: Close to 145D.

*Calyx*.—Arrangement: Star-shaped calyx with five fused sepals. Sepal length: About 1.1 cm. Sepal width: About 1 mm. Sepal shape: Ligulate. Sepal apex: Acute. Sepal margin: Entire. Sepal texture, upper and lower surfaces: Pubescent, coarse. Sepal color, upper and lower surfaces: Close to 146A and 145B.

*Peduncles*.—Length: About 4.7 cm. Diameter: About 2 mm. Strength: Strong. Texture: Pubescent. Color: Close to 143C.

*Pedicels*.—Length: About 0.5 mm. Diameter: About 0.5 mm. Strength: Strong. Texture: Smooth, glabrous. Color: Close to 144C.

*Reproductive organs*.—Stamens: Quantity and arrangement: About four per flower, adnate to corolla tube. Anther length: About 0.6 mm. Anther shape: Oval. Anther color: Close to N144B. Pollen amount: Moderate. Pollen color: Close to 1B. Pistils: Quantity: One per flower. Pistil length: About 1.7 cm. Stigma shape: Bi-parted; fimbriate. Stigma color: Close to 144B. Style length: About 1.6 cm. Style color: Close to 144D. Ovary color: Close to 144B.

Fruits and seeds: Fruit and seed development has not been observed on plants of the new *Verbena*.

Temperature tolerance: Plants of the new *Verbena* have been observed to tolerate temperatures from about 5° C. to about 40° C.

Pathogen & pest resistance: Plants of the new *Verbena* have not been observed to be resistant to pathogens and pests common to *Verbena* plants.

It is claimed:

1. A new and distinct *Verbena* plant named 'Duempamech' as illustrated and described.

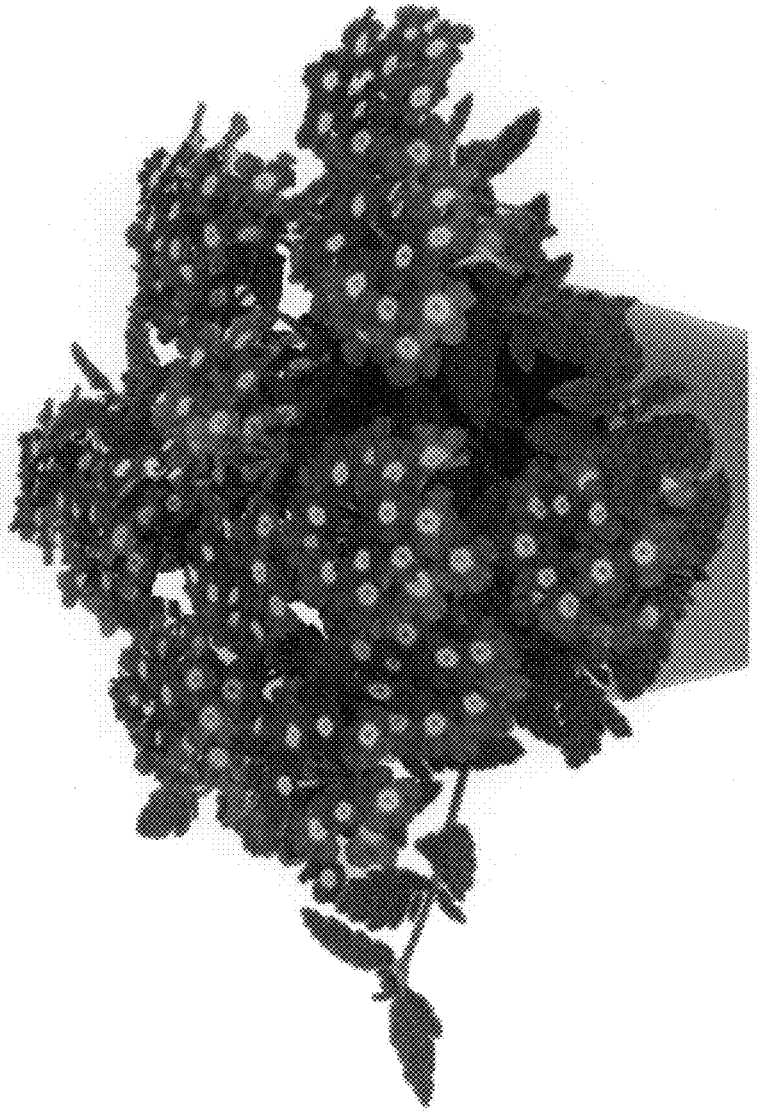

* * * * *